United States Patent [19]
Palmer et al.

[11] Patent Number: 5,235,102
[45] Date of Patent: Aug. 10, 1993

[54] CATALYTIC DISTILLATION USING RIGID, CELLULAR MONOLITHS AS CATALYST-PACKING MATERIAL

[75] Inventors: David A. Palmer, Naperville; Gary P. Hagen, West Chicago, both of Ill.

[73] Assignee: Amoco Corporation, Chicago, Ill.

[21] Appl. No.: 616,227

[22] Filed: Nov. 20, 1990

[51] Int. Cl.$^5$ .................... C07C 53/08; C07C 51/42; B01J 70/10
[52] U.S. Cl. .................... 562/607; 562/606; 203/DIG. 6; 502/527
[58] Field of Search .................. 203/DIG. 6; 567/607; 502/527

[56] References Cited

U.S. PATENT DOCUMENTS

| | | | |
|---|---|---|---|
| 2,936,321 | 5/1980 | Mercier | 562/607 |
| 4,185,027 | 1/1980 | Logan | 562/606 |
| 4,420,612 | 12/1983 | Aiba et al. | 562/607 |
| 5,057,468 | 10/1991 | Adams | 203/DIG. 6 |

OTHER PUBLICATIONS

Patil et al, ACS Symposium Series No. 368 (Jun. 5-11, 1988), applicant's citing.

*Primary Examiner*—Jose' G. Dees
*Assistant Examiner*—Keith MacMillan
*Attorney, Agent, or Firm*—Thomas E. Nemo; Wallace L. Oliver; Frank J. Sroka

[57] ABSTRACT

There is provided a process for the conversion of a feedstream comprising gaseous and/or liquid feed materials to a desired products by means of catalytic distillation employing a catalyst-packing material comprising a rigid, cellular monolith or a rigid, cellular monolith coated with a catalytically-active material.

Preferred rigid, cellular monoliths are ceramic honeycomb monoliths.

4 Claims, 1 Drawing Sheet

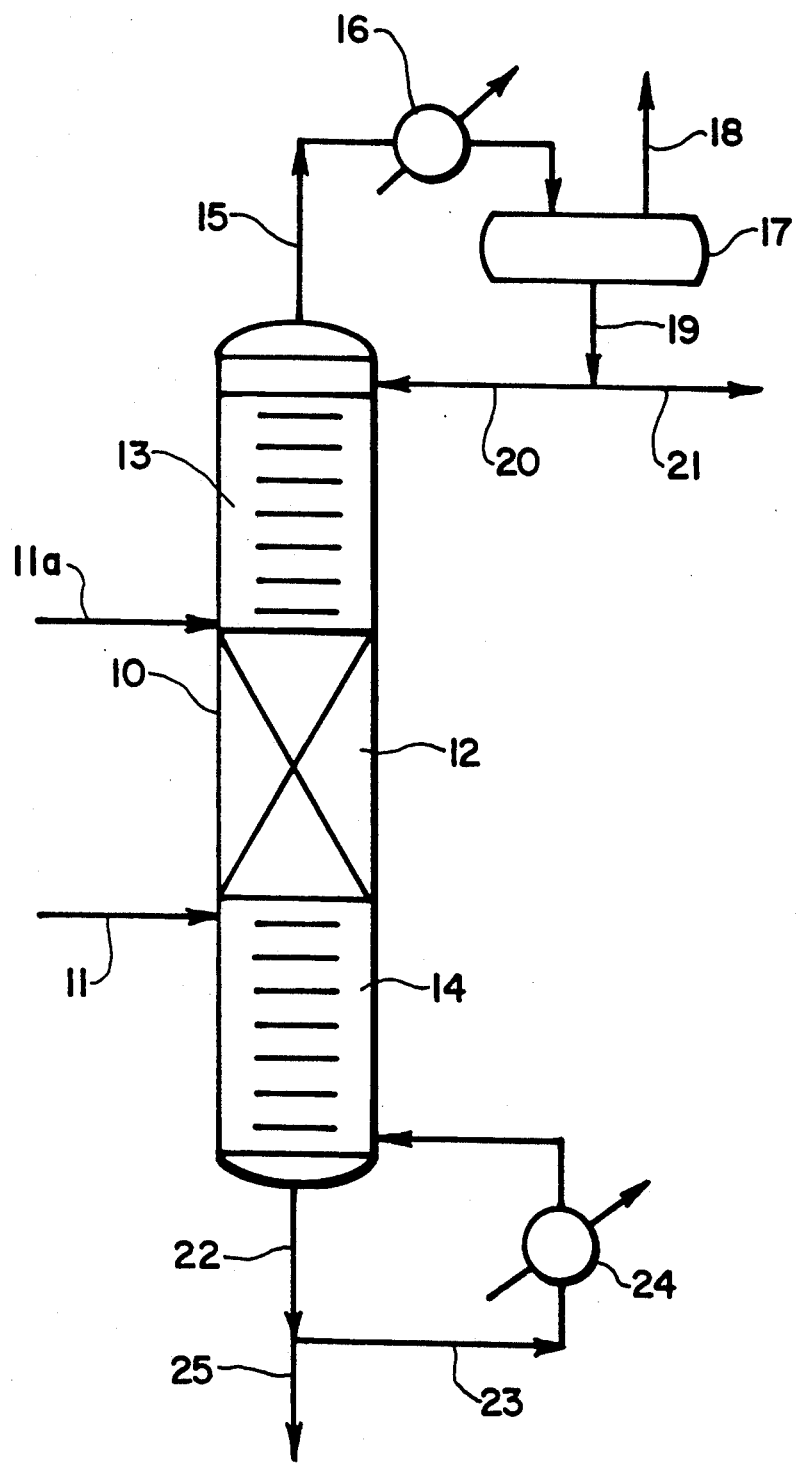

CATALYTIC DISTILLATION USING RIGID, CELLULAR MONOLITHS AS CATALYST-PACKING MATERIAL

CROSS-REFERENCE TO RELATED APPLICATION

This application is being filed concurrently with U.S. application Ser. No. 07/616,213, U.S. Pat. No. 5,113,015 which is directed to a process for recovering acetic acid from methyl acetate wherein the methyl acetate is hydrolyzed to methanol and acetic acid via catalytic distillation.

BACKGROUND OF THE INVENTION

1. Field of the Invention

This invention relates to the conversion of liquid organic materials to suitable products by means of catalytic distillation. More particularly, it relates to an improved catalyst-packing material for use in catalytic distillation and to the processes using such catalyst-packing material.

2. Description of Prior Art

It is known that some reactions may be carried out by means of catalytic distillation. In catalytic distillation, reaction and separation are carried out simultaneously in a distillation column.

In U.S. Pat. No. 4,215,011, Smith, Jr, discloses a method for the separation of an isoolefin, preferably having four to six carbon atoms, from streams containing mixtures thereof with the corresponding normal olefin, wherein the mixture is fed into a reaction-distillation column containing a fixed-bed, acidic cation exchange resin and contacted with the acidic cation exchange resin to react the isoolefin with itself to form a dimer and the dimer is separated from the normal olefin, the particulate catalytic material, i.e., the acidic cation exchange resin, being contained in a plurality of closed cloth pockets, which pockets are arranged and supported in the column by wire mesh.

In U.S. Pat. No. 4,443,559, Smith, Jr, discloses a catalytic distillation structure which comprises a catalyst component associated intimately with or surrounded by a resilient component, which component is comprised of at least 70 vol % open space for providing a matrix of substantially open space. Examples of such resilient component are open-mesh, knitted, stainless wire (demister wire or an expanded aluminum); open-mesh, knitted, polymeric filaments of nylon, Teflon, etc; and highly-open structure foamed material (reticulated polyurethane).

It has been shown by Patil, et al, in a paper given in ACS Symposium Series No. 368 in Toronto, Ontario, Canada Jun. 5-11, 1988) and printed in ACS Symposium Series No. 368, PERSPECTIVES IN MOLECULAR SIEVE SCIENCE, Flank and Whyte, Jr, Editors (1988), American Chemical Society, that a cordierite ceramic honeycomb washcoated with silicate is a suitable catalyst for methanol conversion. Patil, et al, pointed out that an active zeolite catalyst may be washcoated on ceramic honeycomb substrates and that such technique has been used widely in automotive emissions control, woodstove combustors, control of volatile organic emissions from organic solvents, ozone abatement in jet aircraft passenger cabins, and $NO_x$ abatement from industrial emissions. Patil, et al, noted the lack of exploitation of washcoats of zeolite catalysts in the chemical process industries.

Now it has been found that a rigid, cellular monolith or a coated, rigid, cellular monolith can be used suitably as the catalyst-packing material in processes involving catalytic distillation.

SUMMARY OF THE INVENTION

According to the invention, there is provided a process for the conversion of one or more organic materials to one or more selected products, wherein a feedstream comprising the material or materials is passed into a vertical distillation column containing in a catalyst zone a catalyst-packing material comprising a rigid, cellular monolith and is contacted with the catalyst-packing material to convert the material or materials to the desired product or products, desired product or products are separated concurrently from the feedstream, and the desired product or products are withdrawn from the column at points above and/or below said catalyst zone.

In this improved process, the improvement comprises using as the catalyst a catalyst-packing material comprising a rigid, cellular monolith.

Examples of such rigid, cellular monoliths are ceramic honeycomb monoliths selected from cordierite, mullite, and cordierite-mullite and such honeycomb monoliths coated with an active catalytic material.

BRIEF DESCRIPTION OF THE DRAWING

The accompanying FIGURE is a simplified diagram of a catalytic distillation column.

DETAILED DESCRIPTION OF THE INVENTION AND SPECIFIC EMBODIMENTS

The process of the present invention is a process for the conversion of one or more gaseous and/or liquid materials to a desired product or products, wherein the conversion occurs in the presence of a catalyst-packing material in a vertical distillation column. The process employs the unit operating that is identified as "catalytic distillation". In catalytic distillation, a section of a distillation unit or column is used to carry out simultaneously reaction and separation. As a result, equilibrium-limited reactions may be conducted without an external recycle stream.

The catalyst-packing material is a material that serves not only as a catalyst, but also as a packing for the distillation or separation function. Therefore, it has a catalytic function, as well as a distillation packing function. The catalyst-packing material must have a shape and be installed in the distillation column in such a way that there is sufficient open area for gas and liquid flow. The catalyst-packing material must be capable of providing a geometric arrangement which will function as both reaction and distillation sites. In addition, the arrangement in the catalyst bed must furnish an amount of free space in the catalyst bed to permit adequate liquid-phase surface contact and vapor-phase distillation, while providing concurrent separation of the material in the column by the distillation into liquid and vapor phases.

In prior-art catalytic distillation processes, the catalyst-packing material has been employed in the conventional distillation packing shapes of Rashig rings, Pall rings, and saddles and as a particulate catalytic material contained in a plurality of closed cloth pockets which are arranged and supported in the column by wire mesh.

The shape of the catalyst-packing material must be such that it functions as a distillation packing, i.e., it increases the resolution of the distillation.

The catalytically-active material of the catalyst-packing material employed in catalytic distillation may be any material which is suitable for the reaction being conducted. For example, it may be an acid catalyst, or a basic catalyst, or a catalytic metal or its oxide or halide. In addition, it must be heterogeneous with the fluids in the system.

It has now been found that rigid, cellular monoliths are suitable for use as catalyst-packing material in catalytic distillation. Such monoliths will provide sufficient open or free space in the catalyst bed to allow for the distillation function. They may be fabricated from a material that is catalytically active for the desired reaction. Alternatively, they may be coated with a catalytically-active material. For example, they may be made from a molecular sieve or they may comprise rigid, ceramic honeycomb monoliths coated with a molecular sieve, such as silicalite.

The structure of the monolith must be rigid and cellular. It is contemplated that the structure have a cell density that is at least about 5 cells per sq in and a surface area that is consistent with a low pressure drop in the column containing the catalyst-packing material. As cell density increases, surface area increases.

Typically, cell density will fall within the range of about 5 cells per sq in to about 1,000 cells per sq in; preferably, within the range of about 9 cells per sq in to about 400 cells per sq in; and more preferably, within the range of about 100 cells per sq in to about 200 cells per sq in.

Suitable rigid, cellular monoliths are ceramic honeycomb monoliths. Such ceramic honeycomb monoliths are manufactured by the Corning Company under the brand name of "Celcor" and are produced with cell densities of 9, 16, 25, 50, 100, 200, 300, and 400 cells per sq in. The length is typically five or six inches long. The Celcor products are made from cordierite (2 MgO.2Al$_2$O$_3$.5 SiO$_2$), mullite (3Al$_2$O$_3$.SiO$_2$), and cordierite mullite. These, as well as other suitable ceramic monoliths, may be used in the preparation of catalyst-packing material for use in the separation vessels of the present invention. However, it is contemplated that other rigid materials are also suitable for use as such catalyst-packing material.

Consequently, the monolith can be fabricated from various materials, such as, steel, aluminum, copper, titanium, and other metals. It can also be made from polymers, ceramic materials, alumina, silica-alumina, and a variety of other metal oxides or mixed metal oxides, and molecular sieves. The alumina, silica-alumina, and molecular sieves are materials which provide catalytic activity for various reactions. Therefore, a monolith made from one of these latter materials could be used as catalyst-packing material where those reactions that use such a catalytic material are involved.

Alternatively, the rigid, cellular monolith can be coated with a catalytic amount of a material that is catalytically active for the desired reaction. In other words, the surface of the monolith would be coated with the catalytically-active material. The term "catalytic amount" is used herein to indicate that the amount is sufficient to catalyze the reaction for which the catalytic material is being used. If an acidic catalyst were needed, for example, a rigid, ceramic honeycomb monolith fabricated from cordierite, mullite, or cordierite-mullite and having its surface coated with phosphoric acid, sulfuric acid, an acidic cation exchange resin, a molecular sieve, such as silicalite, or some other type of catalyst might be a suitable catalyst-packing material.

Typically, the material that is coated on the surface of the monolith will be present in the catalyst-packing material in an amount that is within the range of about 0 wt % to about 10 wt %, based on the total weight of the composition. Preferably, the catalytically-active material will be present as a coating in an amount that is within the range of about a trace to about 5 wt %, based on the total weight of the composition.

The coating may be applied as a washcoat to the rigid, cellular monolith. Such treatment may involve the use of a binder, as described in the Patil, et al, paper mentioned hereinabove as prior art.

Cordierite is a typical rigid, ceramic honeycomb monolith. It is partially porous and has a surface area that falls within the range of about 23 sq ft per cu ft to about 70 sq ft per cu ft. Its cell structure has cell sizes ranging from about 50 cells per sq in to about 400 cells per sq in.

This catalyst-packing material furnishes a particularly advantageous configuration. Each channel is vertical and provides considerable area for vapor-liquid equilibrium. As the reaction proceeds in the catalytic zone, the heat generated by the reaction is consumed efficiently via vaporization of the downflowing reflux. It is contemplated that catalyst activity would be limited by very small pore diffusion limitations. Each block is square; therefore, there is no need to cover empty spaces from layer to layer. The maximum height of each unit is about six inches.

As is shown in the examples hereinafter, a catalyst-packing material comprising cordierite having its surface coated with silicalite is suitable for use in the catalytic distillation operation wherein methyl acetate is hydrolyzed to methanol and acetic acid. It is to be understood that this is not the sole reaction for which the process of the present invention is applicable. It is contemplated that the technique employing the rigid, cellular monoliths as catalyst-packing material is suitable for other reactions, inter alia, toluene disproportionation to benzene and xylenes, metathesis of different olefins, the production of ethylene glycol from ethylene oxide and water, the production of ethylbenzene from ethylene and benzene, the production of terephthalaldehyde from p-xylene and oxygen, the production of isophthalaldehyde from m-xylene and oxygen, the production of isopropanol from propylene and water, the production of propylene from isopropanol, the production of ethanol from ethylene and water, the production of styrene from alpha-hydroxy ethylbenzene, and the production of para hydroxy styrene from 4(alpha-hydroxyethyl)phenol. It is suitable for the production of ethylene from ethanol, cumene from propylene and benzene, nonene from propylene, dodecene from ethylene or propylene, styrene from benzene and acetylene, styrene from benzene, ethylene, and oxygen, the production of linear alphaolefins, the production of acetic acid from methanol, vinyl acetate from acetic acid, ethylene, and oxygen, vinyl acetate from acetic acid and acetylene, the production of methyl amines, ethyl amines, cresols, and ethylene diamine, the production of methyl-t-butyl ether from isobutylene and methanol, ethyl t-butyl ether from isobutylene and ethanol, methyl pentyl ether from $C_5$-olefins and methanol, dimerizations, oligomerizations, paraffin isomerizations, and paraffin dehydrogenations.

In general, the potential applications for the process of the present invention are quite numerous. The catalyst-packing material is suitable for acidic reactions, basic reactions, oxidation reactions, reduction reactions, and organo-metallic catalyzed or directed reactions depending upon the natures of the monolith and the coating.

Typical examples of appropriate acidic reactions are the preparation of ethanol from ethylene and water, the preparation of ethylene from ethanol, acetic acid and methanol from methyl acetate and water, methyl t-butyl ether from isobutylene and methanol, ethyl-t-butyl ether from isobutylene and ethanol, methyl-pentyl ether from $C_5$-olefins and methanol, ethers from alcohols, such as dimethyl ether from methanol, isoprene from acetone and acetylene, and methyl vinyl ether from methanol and acetylene.

Examples of oxidation reactions are the production of terephthalaldehyde from para-xylene and oxygen and the production of isophthaladehyde from m-xylene and oxygen.

Examples of organo-metallic reactions are metathesis of different olefins, nonene from propylene, dodecene from ethylene or propylene, and styrene from benzene and acetylene. The latter three reactions can also be acidic reactions.

In general, when the catalyst-packing material in the present invention becomes deactivated, it can be reactivated by treatment in air or another oxygen-containing gas at a temperature within the range of about 371° C. (700° F.) to about 538° C. (1,000° F.) for a period of at least about 0.5 hr.

Optionally, original or fresh catalyst-packing material may receive a similar treatment prior to use.

The catalyst-packing material in the catalyst zone of the process of the present invention may be supplemented in the column with trays or conventional packing above or below the catalyst zone in order to minimize the volume of catalyst-packing material that is needed. Many reactions could require an infinite amount of catalyst to go to completion. However, catalytic distillation avoids that, as either reflux or reboiling of the reactant brings it once more in contact with the catalytic or reaction zone.

According to the present invention there is provided a process for the conversion of one or more feed materials selected from gases and liquids to one or more desired products, which process comprises introducing a feedstream comprising said feed materials into a vertical distillation column having a catalyst zone containing as a catalyst a catalyst-packing material comprising a rigid, cellular monolith, contacting said feedstream with said catalyst-packing material to convert at least a portion of said feed materials to said desired products, separating said desired products from said feedstream, and withdrawing said desired products from said column at points above, below, or above and below said catalyst zone, said contacting and said separating being carried out coextensively in said column.

In this improved process for the conversion of one or more feed materials selected from gases and liquids wherein a feedstream comprising said feed materials is introduced into a vertical distillation column having a catalyst zone containing a catalyst-packing material as a catalyst for the conversion of said feed materials to one or more desired products and is contacted with said catalyst-packing material to convert at least a portion of said feed materials to said desired products, said desired products are separated from said feedstream concurrently with the contacting of said feedstream with said catalyst-packing material, and said desired products are withdrawn from said column at points above, below, or above and below said catalyst zone, the improvement which comprises employing as said catalyst-packing material a catalyst-packing material comprising a rigid, cellular monolith.

The accompanying figure represents a typical embodiment of the process of the present invention. This simplified diagram does not show various pieces of auxiliary equipment, such as some heat exchangers, pumps, valves, and the like. However, one skilled in the art would recognize easily where such equipment would be located and when they would be used.

Referring to this figure, column 10 is a vertical distillation column. A feedstream comprising a gaseous or liquid material is introduced into column 10 via line 11 or line 11a. Typically, a gas, such as hydrogen, carbon monoxide, or a halogen, would be introduced through line 11 below the catalyst zone. Column 10 contains catalyst zone 12, which contains catalyst-packing material, which may be present in the form of one or more beds. The catalyst-packing material is that which will catalyze the conversion of the gaseous or liquid feed materials to desired products. For the process of the present invention, the catalyst-packing material comprises rigid, cellular monoliths, which are described hereinabove.

As represented in the figure, the feedstream is introduced into the column 10 at a point below the catalyst zone. Depending upon the reaction occurring in the catalyst zone and the reactants and products involved, the feed may be introduced into the column at a point in the catalyst zone, at a point above the catalyst zone, at a point below the catalyst zone, or at points both above and below the catalyst zone with different feeds. The feed may be introduced also with the reflux when trays or other separating devices are not present above the catalyst zone.

The column may have trays above the catalyst zone, as shown by upper zone 13 of the column, and/or trays below the catalyst zone, as represented by lower zone 14. Alternatively, suitable conventional packing, such as Rashig rings, Pall rings, saddles, or structured packing, such as Flexipac ®, may be used in place of the trays in either the upper zone 13 or the lower zone 14.

At least a portion of the feed materials are converted to a desired product in catalyst zone 12 while concurrently this heavier product is separated from the lighter material in the column 10. The lighter products and non-condensable materials pass up through upper zone 13 and out of the column 10 via line 15. On the other hand, the heavier products and other heavier material pass down through the column through lower zone 14.

The lighter and non-condensable materials pass through line 15 and condenser 16 into condensate drum 17 where the condensed material is separated from the non-condensables. The non-condensables are removed from the system via line 18. The condensed material is passed from condensate drum 17 via line 19, a portion of said condensed material being returned to column 10 via line 20 as reflux and, if needed, a portion is withdrawn from the system via line 21 as light product.

The heavier, i.e., the higher-boiling, material in column 10 is passed from lower zone 14 out of column 10 by way of line 22. A portion thereof is passed through line 23 and reboiler 24 into column 10. Product is removed from the system via line 25.

The process of the present invention is quite suitable for a reaction wherein the products are both lower- and higher-boiling material than those of the feedstream, and hence, can be separated from the feed material via distillation.

The following examples are being presented to facilitate an understanding of the present invention. They are being presented for the purpose of illustration and are not intended to limit the scope of the present invention.

EXAMPLE 1

In this run, Run No 1, methyl acetate was hydrolyzed to acetic acid and methanol.

The apparatus employed in this run comprised a column connected to a 3-neck flask. A condenser was connected to the column at a point near the top of the column. The flask served as a boiler and was encased by a Variac heater. The column contained 10.2 gm of catalyst, i.e., catalyst-packing material, in a tube that was 12.7 mm in inside diameter. The catalyst bed, made up of 3 equivalent sections, was 15.6 cm in height. The catalyst volume was 19.8 cu cm. Nitrogen was slowly added to the column at a point above the catalyst bed for pressure control. A furnace surrounded the column at the location of the catalyst bed. The boiler was maintained at a temperature of 100° C. (212° F.) and the catalyst bed was maintained at a temperature of 112° C. (234° F.). The portion of the column above the catalyst bed was not insulated. The uninsulated section provided a large amount of reflux to the catalyst.

A volumetric funnel and stopcock were located between the bottom of the condenser and the three-neck flask.

The vapors that escaped the column were primarily methyl acetate. They were condensed and returned through the volumetric funnel and stopcock to the three-neck flask.

A 10.2-gm portion of catalyst comprising silicalite coated on cordierite honeycombs and obtained from Corning Company (Corning Code 9475) was charged to the column.

Initially, a feed comprising 35 ml of methyl acetate and 100 ml of water was charged to the flask. Methyl acetate was added continuously to the flask, at a rate of 0.14 ml per min for the first 90 minutes and then at a rate of 0.1 ml per min up until the 280-minute point in time.

Initially, the selectivity to acetic acid was zero, while the selectivity to acetone was 100%. After two hours, the selectivity to acetic acid was 60%; after three hours, 86%; after six hours, 97.6% at 98.7% conversion; and after nine hours, 99.2% at 99.2% conversion. By that time, selectivity to acetone was only 0.8% and the catalyst was lined out in the high acetic acid selectivity mode.

Accordingly, this run, Run No 1, illustrates the very high acetic acid selectivities that can be achieved after the catalyst has been lined out. The acetic acid selectivity became very high after a reasonably short time.

EXAMPLE II

In this run, Run No 2, methyl acetate was hydrolyzed to methanol and acetic acid.

The apparatus was made up of a column connected to a U-bend tube inserted in a heated water pool, which simulated a reboiler. A catalyst bed, similar to that described in Example I, was located in the column. A condenser was mounted above the column, so that all reflux was returned to the catalyst zone.

A 10.2-gm portion of catalyst was charged to the column. The catalyst comprised silicalite coated on cordierite honeycombs obtained from Corning Company (Corning Code 9475). The methyl acetate and water were introduced into the system above the reaction zone in a ratio of 1.1:1. The methyl acetate was pumped at a rate of 0.0488 ml/min (0.00089 gm-mole/min), while the water was pumped at a rate of 0.0176 ml/min (0.00098 gm-mole/min).

The data obtained from Run No 2 are presented hereinbelow in Table 1.

TABLE I

| Time, min | Conversion, % | METHYL ACETATE CONVERSION % Selectivity to | | | Temp., °C. | |
|---|---|---|---|---|---|---|
| | | Acetic Acid | Acetone | Other | Reaction | Highest |
| 40 | 8.9 | 99.8 | 0.0 | 0.2 | 187 | 187 |
| 80 | 25.8 | 98.2 | 0.99 | 0.81 | 194 | 200 |
| 120 | 22.9 | 99.2 | 0.0 | 0.82 | 140 | 171 |
| 160 | 29.8 | 88.7 | 9.5 | 1.79 | 167 | 221 |
| 200 | 25.0 | 95.0 | 3.3 | 1.73 | 204 | 216 |
| 240 | 27.9 | 88.6 | 5.5 | 1.31 | 172 | 204 |
| 280 | 26.6 | 91.0 | 6.3 | 2.62 | 157 | 212 |
| 320 | 28.4 | 91.2 | 6.3 | 2.48 | 171 | 171 |
| 360 | 24.0 | 98.0 | 0.9 | 1.06 | 130 | — |
| 400 | 30.4 | 88.9 | 8.8 | 2.31 | 182 | — |
| 440 | 32.0 | 78.7 | 17.4 | 3.92 | 190 | 214.5 |

In this particular run, the conversions were normally between 25% and 32%. The selectivities to acetic acid were high. However, the selectivities to acetone were greater than desired. The reaction seemed to be more selective to acetic acid at lower temperatures. The high acetone levels were due probably to the higher ratio of methyl acetate to water. Increased water levels will probably result in lower selectivities to acetone.

The results of the above tests demonstrate that a catalyst-packing material comprising a rigid, cellular monolith, such as a ceramic honeycomb monolith, coated with silicalite, is suitable for catalytic distillation operations wherein a liquid material is converted efficiently to a desired product, e.g., methyl acetate is converted to acetic acid.

What is claimed is:

1. A process for the catalytic reaction and distillation of gaseous and/or liquid methyl acetate to acetic acid and methanol, which process comprises introducing a feedstream comprising methyl acetate into a vertical distillation column having a catalyst zone containing a heterogeneous ceramic honeycomb coated with silicalite catalyst serving as a catalyst-packing material and comprising a rigid, cellular monolith in the form of channels mounted vertically for gas and liquid flow, contacting said feedstream with said catalyst-packing material in the presence of water to convert at least a portion of said methyl acetate to said acetic acid and said methanol, separating said acetic acid from said feedstream by distillation into liquid and vapor phases, withdrawing said acetic acid from said vertical distillation column at a point below said catalyst zone, said contacting and said separating being carried out coextensively in said vertical distillation column.

2. The process of claim 1, wherein said rigid, cellular monolith is a ceramic honeycomb monolith having coated on its surface a catalytic amount of silicalite.

3. The process of claim 2, wherein said ceramic honeycomb monolith comprises a member selected from the group consisting of cordierite, mullite, and cordierite-mullite.

4. The process of claim 3, wherein said ceramic honeycomb monolith comprises cordierite.

* * * * *